(12) United States Patent
Swanson

(10) Patent No.: US 6,410,643 B1
(45) Date of Patent: *Jun. 25, 2002

(54) SOLID PHASE SYNTHESIS METHOD AND REAGENT

(75) Inventor: Melvin J. Swanson, Carver, MN (US)

(73) Assignee: SurModics, Inc., Eden Prairie, MN (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/521,552

(22) Filed: Mar. 9, 2000

(51) Int. Cl.⁷ .................. C08H 21/00; C08H 21/02; C08H 21/04
(52) U.S. Cl. .................. 525/54.11; 536/25.3; 536/126; 435/DIG. 1; 435/DIG. 22; 435/DIG. 46; 435/DIG. 47; 435/DIG. 49
(58) Field of Search ................ 525/54.11; 536/25.3, 536/126; 435/DIG. 1, DIG. 22, DIG. 46, DIG. 47, DIG. 49

(56) References Cited

U.S. PATENT DOCUMENTS

| | | | |
|---|---|---|---|
| 4,722,906 A | 2/1988 | Guire | |
| 4,753,985 A | 6/1988 | Rosevear et al. | |
| 4,979,959 A | 12/1990 | Guire | |
| 5,002,582 A | 3/1991 | Guire | |
| 5,217,492 A | 6/1993 | Guire et al. | |
| 5,296,572 A | 3/1994 | Sparrow et al. | |
| 5,470,916 A | 11/1995 | Righetti et al. | |
| 5,480,790 A | 1/1996 | Tischer et al. | 435/188 |
| 5,487,888 A | 1/1996 | Mandeville, III et al. | 424/78.1 |
| 5,512,329 A | 4/1996 | Guire et al. | |
| 5,563,056 A | 10/1996 | Swan et al. | |
| 5,637,460 A | 6/1997 | Swan et al. | |
| 5,714,360 A | 2/1998 | Swan et al. | |
| 5,741,551 A | 4/1998 | Guire et al. | |
| 5,744,515 A | 4/1998 | Clapper | |
| 5,783,502 A | 7/1998 | Swanson | |
| 5,785,832 A | 7/1998 | Chiari et al. | |
| 5,858,653 A | 1/1999 | Duran et al. | |
| 5,942,555 A | 8/1999 | Swanson et al. | |
| 6,057,100 A | 5/2000 | Heyneker | 435/6 |

FOREIGN PATENT DOCUMENTS

| | | |
|---|---|---|
| EP | 0 288 310 A2 | 10/1988 |
| EP | 0 599 741 A1 | 6/1994 |
| EP | 0 609 891 A2 | 9/1994 |
| WO | WO 93/11174 | 6/1993 |
| WO | WO 95/27263 | 10/1995 |
| WO | WO 95/27264 | 10/1995 |
| WO | WO 95/27265 | 10/1995 |
| WO | WO 95/27266 | 10/1995 |
| WO | WO 95/27267 | 10/1995 |
| WO | WO 95/27268 | 10/1995 |
| WO | 97/16462 | * 5/1997 |
| WO | WO 97/19283 | 5/1997 |
| WO | WO 97/21082 | 6/1997 |
| WO | WO 97/27226 | 7/1997 |
| WO | WO 98/01419 | 1/1998 |
| WO | WO 98/06627 | 2/1998 |
| WO | WO 98/39099 | 9/1998 |
| WO | WO 98/41534 | 9/1998 |
| WO | WO 98/56506 | 12/1998 |
| WO | WO 99/04895 | 2/1999 |
| WO | WO 99/11692 | 3/1999 |
| WO | WO 99/16907 | 4/1999 |
| WO | WO 99/47176 | 9/1999 |

OTHER PUBLICATIONS

Woodbury, CP Jr., et al., "Methods of Screening Combinatorial Libraries Using Immobilized or Restrained Receptors"*Journal of Chromatography B*, vol. 725(1), pp. 114–137 (1999).

Labadie, J., "Polymeric Supports for Solid Phase Synthesis", *Current Opinion in Chemical Biology*, vol. 2, pp. 346–352 (1998).

Righetti, P. et al., "Electrophoresis Gel Media: The State of the Art", *Journal of Chromatography B*, vol. 699, pp. 64–75 (1996).

"Solid–Phase Resins", http://www.argotech.com/resins/files/solid.htm, 3 pgs., (Printed Jun. 2, 1999).

Woodbury, CP Jr. et al., "Methods of Screening Combinatorial Libraries Using Immobilized or Restrained Receptors", *J. Chromatogr B Biomed Sci Appl*, vol. 725, No. 1, (Abstract only) (Apr. 2, 1999).

Kanda, P. et al., "Synthesis of polyamide supports for use in peptide synthesis and as peptide–resin conjugates for antibody production", *Int. J. Peptide Protein Res.*, vol. 38, No. 4., pp. 385–391 (Oct. 1991).

* cited by examiner

*Primary Examiner*—Nathan M. Nutter
(74) *Attorney, Agent, or Firm*—Merchant & Gould P.C.

(57) ABSTRACT

A reagent composition adapted to be coated onto a support surface in order to provide that surface with a high density of reactive groups. The surface, thus coated, can be used for any suitable purpose, and is particularly well suited for use as a solid phase synthesis support surface. The synthesis support surface, in turn, can be used in repetitive and combinatorial syntheses such as the synthesis of polynucleotides, polypeptides and polysaccharides. The polymeric coating can be used to provide increased effective surface area, particularly in situations in which the effective area of the support surface is itself limited, as on the surface of a silicon wafer. In so doing, the polymeric coating provides an optimal combination of such properties as reactive density and surface area or volume.

23 Claims, No Drawings

SOLID PHASE SYNTHESIS METHOD AND REAGENT

TECHNICAL FIELD

In one aspect, the present invention relates to methods, reagents and support surfaces for use in solid phase (e.g., repetitive or combinatorial) synthesis. In another aspect, the invention relates to substituted polyacrylamide reagents. In yet another aspect, the invention relates to reagents for use in modifying support surfaces, and in particular, the use of photochemical means to attach such reagents to such surfaces.

BACKGROUND OF THE INVENTION

Solid phase synthesis has evolved tremendously since the seminal work of R. B. Merrifield in 1963. Typically, the reactions used are the same as ordinary synthesis, with one of the reactants being anchored onto a solid support. Solid phase synthesis can be used, for instance, for the synthesis of polynucleotides, polysaccharides, and polypeptides, as well as other applications in repetitive syntheses and combinatorial chemistry.

The basic advantage of the solid phase technique is that the support (including all reagents attached to it) remains insoluble and is therefore easily separated from all other reagents. Excess reagents, other reaction products and side products, are quickly and efficiently removed upon removal of the solvents. Purification of the solid phase species is rapid and complete as well, and the entire process can be automated.

In recent years, the principles of solid phase synthesis have been applied to a new methodology known as "combinatorial chemistry". Scientists use combinatorial chemistry to create large populations of molecules, or libraries, that can be screened efficiently en masse. By producing larger, more diverse compound libraries, companies increase the probability that they will find novel compounds of significant therapeutic and commercial value. The field represents a convergence of chemistry and biology, made possible by fundamental advances in miniaturization, robotics, and receptor development.

As with traditional drug design, combinatorial chemistry relies on organic synthesis methodologies. The difference is the scope—instead of synthesizing a single compound, combinatorial chemistry exploits automation and miniaturization to synthesize large libraries of compounds. But because large libraries do not produce active compounds independently, scientists also need to find the active components within these enormous populations. Thus, combinatorial organic synthesis is not random, but systematic and repetitive, using sets of chemical "building blocks" to form a diverse set of molecular entities.

There are at least three common approaches to combinatorial organic synthesis. During arrayed, spatially addressable synthesis, building blocks are reacted systematically in individual reaction wells or positions to form separate "discrete molecules." Active compounds are identified by their location on the grid. This method has been applied in scale (as in the Parke-Davis Pharmaceutical "DIVERSOMER" technique), as well as in miniature (as in the Affymax "VLSIPS" technique). The second technique, known as encoded mixture synthesis, uses nucleotide, peptide, or other types of more inert chemical tags to identify each compound.

During deconvolution, the third approach, a series of compound mixtures is synthesized combinatorially, each time fixing some specific structural feature. Each mixture is assayed as a mixture and the most active combination is pursued. Further rounds systematically fix other structural features until a manageable number of discrete structures can be synthesized and screened. Scientists working with peptides, for example, can use deconvolution to optimize, or locate, the most active peptide sequence from millions of possibilities.

On a related subject, surfaces modified to provide reactive groups or other desired functionalities have long been used for performing solid phase syntheses of both polymeric and nonpolymeric molecules. A variety of solid phase resins are commercially available, e.g., those available from Argonaut Technologies, including their line of Polystyrene, ArgoGel™, and ArgoPore™ resins. Along similar lines, published International Patent Application No. WO9727226 ("Highly Functionalized Polyethylene Glycol Grafted Polystyrene Supports"), assigned to Argonaut Technologies, describes polymers and graft copolymers having a backbone of poly(methylsytrene) and side chain polymers of poly (ethylene oxide).

Such supports are also described in JW Labadie ("Polymeric Supports for Solid Phase Synthesis"), *Current Opinions in Chemical Biology* 2:346 (1998). This article describes, for instance, the manner in which functional groups can be introduced into lightly cross-linked polystyrene, using either functional styrene monomers or in a post-functionalization step. In both approaches, however, the functional groups are apparently attached to the polystyrene polymers used to form the support (e.g., bead) itself, e.g., as opposed to being added as a separate coating to a pre-existing support.

The Labadie article also describes the use of PEG-grafted polystyrene, e.g., in the form of the "TentaGel" product prepared by grafting ethylene oxide to hydroxyl-functional polystyrene. The article further describes the manner in which various "shortcomings" associated with PEG grafts resins have been overcome by a graft resin identified as "ArgoGel™" which is designed with a bifurcation at the polystyrene-graft linkage through the use of a polystyrene diol as the base resin. With each of these approaches, the resultant polymers appear to be limited to functional groups at their terminal ends, as opposed to having functional groups in multiple positions along the length of the polymers.

On yet another subject, a variety of polymeric compositions have been described for use as electrophoretic gels. See generally, Righetti, et al., *J. Chromatog. B. Biomed. Sci.* 10;699(1–2):63–75 (1997) which describes recent advances in polyacrylamide gel electrophoresis.

See, for instance, U.S. Pat. No. 5,470,916, for "Formulations for Polyacrylamide Matrices in Electrokinetic and Chromatographic Methodologies". The '916 patent describes formulations obtained via polymerization or co-polymerization of a unique class of monomers.

See also, U.S. Pat. No. 5,785,832, for "Covalently Crosslinked, Mixed-bed Agarose-polyacrylamide Matrices for Electrophoresis and Chromatography", which describes polyacrylamide matrices based on a novel class of N-mono- and di-substituted acrylamide monomers. The '832 patent describes the manner in which mixed-bed matrices of the type polyacrylamide-agarose, covalently linked (crosslinked), are useful in the separation of fragments of nucleic acid, particular DNA, of intermediate size (from 50 to 5,000 base pairs) and of high molecular mass proteins (>500,000 Da). The '832 patent provides covalently-linked polyacrylamide-agarose mixed-bed matrices suitable for use in the separation of fragments of nucleic acids of intermediate size.

Substituted polyacrylamides such as those described above have been restricted to use in preparing electrophoretic gels, and, to the best of Applicant's awareness, have not previously been attached to surfaces, let alone attached for the purpose of providing a solid phase synthetic surface, or by photochemical means.

On a separate subject, the assignee of the present invention has previously described the modification of surfaces for a variety of purposes, and using a variety of reagents. In particular, these reagents generally involve the use of photochemistry, and in particular, photoreactive groups, e.g., for attaching polymers and other molecules to support surfaces. See, for instance, U.S. Pat. Nos. 4,722,906, 4,979,959, 5,217,492, 5,512,329, 5,563,056, 5,637,460, 5,714,360, 5,741,551, 5,744,515, 5,783,502, 5,858,653, and 5,942,555.

SUMMARY OF THE INVENTION

The present invention provides a method for performing solid phase synthesis, the method comprising the steps of:

a) providing a support material providing a surface adapted for use in solid phase synthesis, b) providing a polymeric reagent formed by the polymerization of monomers of the formula:

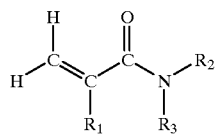

wherein $R_1$ represents hydrogen or $C_1$–$C_6$ alkyls, and wherein $R_2$ and $R_3$, independently among them, represent hydrogen, $C_1$–$C_6$ alkyls or phenyls containing one or more reactive substituents selected from

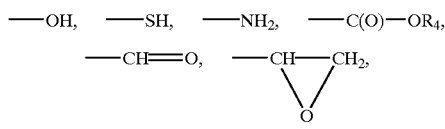

$OR_5$, or $SR_5$ (where $R_4$ is a $C_1$–$C_6$ alkyl or a heterocyclic ring containing one or more nitrogen atoms and $R_5$ is a $C_1$–$C_6$ alkyl or phenyl containing one or more reactive substituents selected from

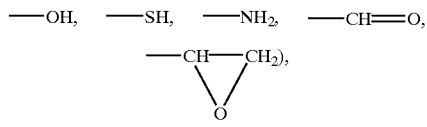

c) applying the reagent to the support surface and covalently attaching the polymeric reagent to the support surface, d) providing a first reactive monomer adapted for solid phase synthesis, e.g., selected from nucleotides and amino acids, the monomer comprising a corresponding group thermochemically reactive with the bound reactive substituent, and preferably also comprising one or more groups reactive with a subsequent, second monomer unit in the course of solid phase synthesis, e) contacting and reacting the first monomer with the polymeric reagent upon the support surface under conditions suitable to react the corresponding group with the bound reactive substituent, thus providing a growing polymeric chain, and f) providing and sequentially attaching subsequent monomers to the growing polymeric chain to obtain a desired polymeric product.

Once formed in this manner, the resultant polymeric product can either be retained and used in situ (e.g., in its bound condition), or it can be cleaved and removed from its position upon the support, in order to be used in a different manner.

In another aspect, the present invention provides a polymeric reagent composition adapted to be coated onto a support surface in order to provide that surface with a high density of reactive groups. The surface, thus coated, can be used for any suitable purpose, and is particularly well suited for use as a solid phase synthesis support surface. The synthesis support surface, in turn, can be used in repetitive and combinatorial syntheses such as the synthesis of polynucleotides, polypeptides and polysaccharides. The polymeric coating can be used to provide increased effective surface area, particularly in situations in which the effective area of the support surface is itself limited, as on the surface of a bead or silicon wafer. In so doing, the polymeric coating provides an optimal combination of such properties as reactive group density and surface area or volume.

In a preferred embodiment, the polymer reagent is provided in the form of a hydrophilic or amphiphilic polymeric reagent adapted to be coated onto a support surface via stable covalent bonds in order to provide the surface with a high, but controllable, density of functional groups suitable for solid phase synthesis of peptides, oligonucleotides, other oligomers (e.g., peptide nucleic acids) or nonpolymeric organic compounds.

In a particularly preferred embodiment, the reagent is prepared by the polymerization of one or more functional group-containing monomers of the formula:

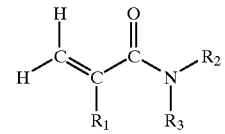

wherein $R_1$ represents hydrogen or $C_1$–$C_6$ alkyls, and wherein $R_2$ and $R_3$, independently among them, represent hydrogen, $C_1$–$C_6$ alkyls or phenyls containing one or more reactive substituents selected from

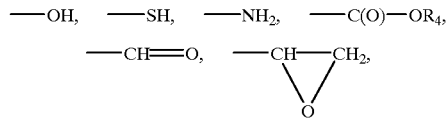

$OR_5$, or $SR_5$ (where $R_4$ is a $C_1$–$C_6$ alkyl or a heterocyclic ring containing one or more nitrogen atoms and $R_5$ is a $C_1$–$C_6$ alkyl or phenyl containing one or more reactive substituents selected from

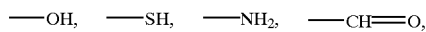

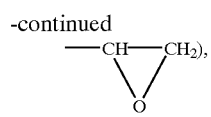

Certain monomers of this type are described, for instance, in Righetti ('832), the disclosure of which is incorporated herein by reference. In one preferred embodiment of the present invention, the polymeric reagent is prepared from monomers that include N-acryloyl-amino-ethoxy-ethanol (AAEE) a highly hydrophilic monomer which is extremely resistant to hydrolysis (Chiari, Micheletti, Nesi, Fazio, Righetti; *Electrophoresis* 15, 1994, 177–186). Other monomers of this type are described in U.S. Pat. No. 5,858,653 the disclosure of which is incorporated herein by reference.

The method and reagent of this invention find particular utility in situations in which it is desired to increase the synthesis capacity without necessarily requiring a corresponding or undue increase in reaction volume. The reagent of the present invention provides a preformed polymer composition in which the polymer molecules can be purified, characterized, and controlled in a manner not heretofore possible.

In a preferred embodiment, the reagent includes the attachment of preformed synthetic polymers to a surface (as distinguished from those formed by polymerization in situ upon the support), and more preferably, the attachment of the preformed polymers by photochemical means. It is also preferred that the functional groups be present at a plurality of positions along the polymer backbone. The number (or average number) and position of functional groups can be controlled by the choice of monomers used to form the polymer, e.g., by the ratio of functional group-containing monomers to "diluent" monomers.

A polymer reagent composition of this invention provides an optimal combination of such properties as swellability, functional group density, reactivity, permeability, hydrophilicity, and hydrolytic stability. In a particularly preferred embodiment, the reagent composition comprises a polymeric derivative providing one or more different reactive groups. The reagent composition can be attached to the surface in any suitable manner, and is preferably covalently attached to the surface, more preferably by the use of photoreactive groups.

Suitable support materials include beads, slides, wafers, films, discs and plates (e.g., microwell plates), prepared from such materials as organosilane-treated glass, organosilane-treated silicon, polypropylene, polyethylene, and polystyrene (optionally cross-linked with divinylbenzene). Additional support materials include grafted polyacrylamide beads, latex beads, dimethylacrylamide beads (optionally cross-linked with N,N'-bis-acryloyl ethylene diamine), glass particles coated with hydrophobic polymers, etc., (i.e., having a rigid or semi-rigid surface). Divinylbenzene-crosslinked, polyethyleneglycol-grafted polystyrene type beads can be used as well.

In a particularly preferred embodiment, the reagent comprises an hydroxyl-substituted polyacrylamide reagent. Such a reagent can be attached to a surface, e.g., photochemically, in any desired manner and concentration, in order to provide the surface with a desired density of reactive (e.g., primary hydroxyl) groups.

A polymer of this invention can be prepared using any suitable means, e.g., by the reaction of monomers providing one or more functional groups with one or more reactive comonomers (e.g., monomers providing a photoreactive group) and/or with one or more non-reactive comonomers (e.g., "diluent" monomers lacking either a photoreactive group or functional group). Those skilled in the relevant art, given the present description, will appreciate the manner in which a polymer of this invention can be synthesized by free radical polymerization using concentrations and ratios of monomers tailored to achieve the desired surface characteristics. Thus the relative and absolute concentrations of functional groups, as well as the molecular weight of the polymer (and extent of branching, etc.), and the means of immobilizing the polymer (such as by the numbers and/or locations of photoactivatable groups along its length) can all be adjusted to optimize performance.

Comonomers having functional groups of varying types and reactivities, can be selected as well. Although not the only determining factor, the length of whatever spacer may be included between a functional groups and the ultimate polymer backbone can have a predictable or determinable effect on the reactivity of the functional group. In addition, relatively inert monomers can be included, in effect as diluent monomers, in order to adjust the density of the functional groups to desired levels and to achieve the desired polymer characteristics, e.g., to adjust its hydrophilic, hydrophobic, or amphiphilic nature, which in turn can affect its solvation characteristics.

Finally, comonomers can also be included that provide reactive groups for immobilizing the polymer onto a surface. Such monomers preferably contain photoactivatable groups, or can include thermochemically reactive groups that can be used to either attach the polymer directly to a corresponding reactive site or group on the surface, or to another reagent that itself provides a photoactivatable group. For example, hydroxyl groups can be activated with a variety of activating agents (e.g., 1,1-carbonyldiimidazole, 2,2,2-trifluoroethanesulfonyl chloride, or 2-fluoro-1-methylpyridinium p-toluenesulfonate). Such reactions can be used to immobilize a hydroxyl polymer onto a surface containing amine groups (e.g., glass coated with 3-aminopropyltriethoxysilane). In this example, any excess activated hydroxyl groups that do not react with amines on the surface can be hydrolyzed back to free hydroxyl groups. The comonomers can also be selected having different polymerization rates, to optimize the distribution of comomomers in the polymer. Optionally, or in addition, comonomer distribution can be controlled and affected by the preparation and use of block copolymers.

Hydrophilic or amphiphilic polymers are also provided, having means for immobilizing to a surface via stable covalent bonds and multiple functional groups of the type described herein. Such polymers find particular use for solid phase synthesis of peptides, oligonucleotides, similar type polymers (e.g., peptide nucleic acids) and nonpolymeric organic compounds. The use of presynthesized polymers, e.g., as opposed to grafted polymers or those formed in situ, provides a number of advantages, including the ability to purify and characterize the polymer before immobilization.

In yet another aspect, the invention provides a method of providing reactive groups upon a surface, the method including the step of coating the surface with a reagent composition as described herein. In further aspects, the invention provides a support surface coated with such a reagent composition.

DETAILED DESCRIPTION

In a preferred embodiment, a reagent of this invention is prepared by the polymerization of monomers containing functional groups, optionally and preferably, in combination with other monomers, such as those containing other useful groups, diluent monomers and the like.

In a preferred embodiment, a polymer of the present invention is prepared by polymerizing one or more monomers selected from the group:

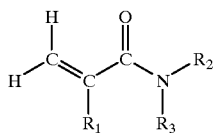

wherein $R_1$ represents hydrogen or $C_1$–$C_6$ alkyls, and wherein $R_2$ and $R_3$, independently among them, represent hydrogen, $C_1$–$C_6$ alkyls or phenyls containing one or more reactive substituents selected from

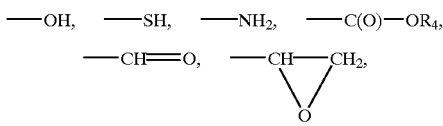

$OR_5$, or $SR_5$ (where $R_4$ is a $C_1$–$C_6$ alkyl or a heterocyclic ring containing one or more nitrogen atoms and $R_5$ is a $C_1$–$C_6$ alkyl or phenyl containing one or more reactive substituents selected from

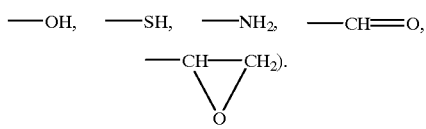

Optionally, and preferably, the resultant polymers are also attached to the surface via photochemical means, e.g., by the incorporation of one or more photogroups into the polymer by means of photogroup-containing copolymerizable monomers.

Comonomers can be selected to provide any desired property or function, including any desired reactivity. Although not the only determining factor, the length of the spacer between the functional groups and the polymer backbone often has an effect on the reactivity of the functional groups.

In addition, "inert" or "diluent" monomers can be used to adjust the density of functional groups to optimal levels and to achieve the desired polymer characteristics, such as hydrophilic or amphiphilic polymers, in order to achieve optimal solvation characteristics. Examples of such monomers include, for instance, acrylamide, N-vinyl pyrrolidone, methacrylamide, N-isopropylacrylamide, N-vinylpyridine, N-vinyl caprolactam, styrene, vinyl acetate, and N-acryloylmorpholine.

A preferred composition of this invention includes one or more pendent latent reactive (preferably photoreactive) groups covalently attached, or adapted to be attached, directly or indirectly, to a copolymerizable monomer. Photoreactive groups are defined herein, and preferred groups are sufficiently stable to be stored under conditions in which they retain such properties. See, e.g., U.S. Pat. No. 5,002,582, the disclosure of which is incorporated herein by reference. Latent reactive groups can be chosen that are responsive to various portions of the electromagnetic spectrum, with those responsive to ultraviolet and visible portions of the spectrum (referred to herein as "photoreactive") being particularly preferred.

Photoreactive groups respond to specific applied external stimuli to undergo active specie generation with resultant covalent bonding to an adjacent chemical structure, e.g., as provided by the same or a different molecule. Photoreactive groups are those groups of atoms in a molecule that retain their covalent bonds unchanged under conditions of storage but that, upon activation by an external energy source, form covalent bonds with other molecules.

The photoreactive groups generate active species such as free radicals and particularly nitrenes, carbenes, and excited states of ketones upon absorption of electromagnetic energy. Photoreactive groups may be chosen to be responsive to various portions of the electromagnetic spectrum, and photoreactive groups that are responsive to e.g., ultraviolet and visible portions of the spectrum are preferred and may be referred to herein occasionally as "photochemical group" or "photogroup".

Photoreactive aryl ketones are preferred, such as acetophenone, benzophenone, anthraquinone, anthrone, and anthrone-like heterocycles (i.e., heterocyclic analogs of anthrone such as those having N, O, or S in the 10-position), or their substituted (e.g., ring substituted) derivatives. Examples of preferred aryl ketones include heterocyclic derivatives of anthrone, including acridone, xanthone, and thioxanthone, and their ring substituted derivatives.

The functional groups of such ketones are preferred since they are readily capable of undergoing the activation/inactivation/reactivation cycle described herein. Benzophenone is a particularly preferred photoreactive moiety, since it is capable of photochemical excitation with the initial formation of an excited singlet state that undergoes intersystem crossing to the triplet state. The excited triplet state can insert into carbon-hydrogen bonds by abstraction of a hydrogen atom (from a support surface, for example), thus creating a radical pair. Subsequent collapse of the radical pair leads to formation of a new carbon-carbon bond. If a reactive bond (e.g., carbon-hydrogen) is not available for bonding, the ultraviolet light-induced excitation of the benzophenone group is reversible and the molecule returns to ground state energy level upon removal of the energy source. Photoactivatible aryl ketones such as benzophenone and acetophenone are of particular importance inasmuch as these groups are subject to multiple reactivation in water and hence provide increased coating efficiency.

The azides constitute an additional preferred class of photoreactive groups and include arylazides ($C_6R_5N_3$) such as phenyl azide and particularly 4-fluoro-3-nitrophenyl azide, acyl azides (—CO—$N_3$) such as benzoyl azide and p-methylbenzoyl azide, azido formates (—O—CO—$N_3$) such as ethyl azidoformate, phenyl azidoformate, sulfonyl azides (—$SO_2$—$N_3$) such as benzenesulfonyl azide, and phosphoryl azides $(RO)_2PON_3$ such as diphenyl phosphoryl azide and diethyl phosphoryl azide. Diazo compounds constitute another class of photoreactive groups and include diazoalkanes (—$CHN_2$) such as diazomethane and diphenyldiazomethane, diazoketones (—CO—$CHN_2$) such as diazoacetophenone and 1-trifluoromethyl-1-diazo-2-pentanone, diazoacetates (—O—CO—$CHN_2$) such as t-butyl diazoacetate and phenyl diazoacetate, and beta-keto-alpha-diazoacetates (—CO—$CN_2$—CO—O—) such as t-butyl alpha diazoacetoacetate. Other photoreactive groups include the diazirines (—$CHN_2$) such as 3-trifluoromethyl-3-phenyldiazirine, and ketenes (—CH=C=O) such as ketene and diphenylketene.

Upon activation of the photoreactive groups, the reagent molecules are covalently bound to each other and/or to the material surface by covalent bonds through residues of the photoreactive groups. Exemplary photoreactive groups, and their residues upon activation, are shown as follows (wherein R and R' can be any non-interfering organic groups).

| Photoreactive | Group | Residue Functionality |
|---|---|---|
| aryl azides | amine | R—NH—R' |
| acyl azides | amide | R—CO—NH—R' |
| azidoformates | carbamate | R—O—CO—NH—R' |
| sulfonyl azides | sulfonamide | R—$SO_2$—NH—R' |
| phosphoryl azides | phosphoramide | $(RO)_2$PO—NH—R' |
| diazoalkanes | new C—C bond | |
| diazoketones | new C—C bond and ketone | |
| diazoacetates | new C—C bond and ester | |
| beta-keto-alpha-diazoacetates | new C—C bond and beta-ketoester | |
| aliphatic azo | new C—C bond | |
| diazirines | new C—C bond | |
| ketenes | new C—C bond | |
| photoactivated ketones | new C—C bond and alcohol | |

The photoactivatable monomers of the invention can be applied to any surface having carbon-hydrogen bonds, with which the photoreactive groups can react to immobilize the resulting polyacrylamide to surfaces. Examples of appropriate substrates include, but are not limited to, polypropylene, polystyrene, poly(vinyl chloride), polycarbonate, poly (methyl methacrylate), parylene and any of the numerous organosilanes used to pretreat glass or other inorganic surfaces.

Polymers of this invention are preferably synthesized by free radical polymerization using concentrations and ratios of monomers that are tailored to achieve the desired surface characteristics. Thus the levels of functional groups, the molecular weight of the polymer and the means of immobilizing the polymer (e.g., by the incorporation of photoactivatable groups), can be adjusted by those skilled in the art to achieve any desired product and/or to optimize the performance or physical-chemical characteristics in one or more respects.

A reagent of the present invention can be used in a variety of ways to provide functionalized support surfaces for use in solid phase synthesis. In one embodiment, the reagent can be packaged and provided separately, and optionally in bulk, to be applied to a surface by the user at the time of use. In another embodiment, the reagent can be applied and covalently bound to a support (e.g., by photochemical means) at the time of manufacturing the support itself, and the resultant coated support material can be packaged and sold in a form substantially ready for use.

TABLE OF STRUCTURES

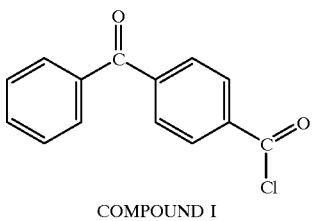

COMPOUND I

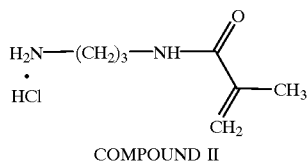

COMPOUND II

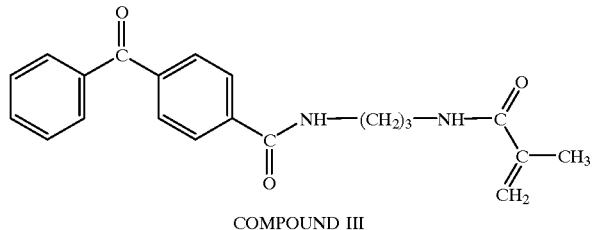

COMPOUND III

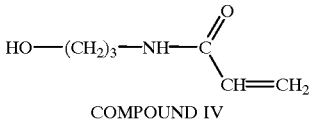

COMPOUND IV

-continued
TABLE OF STRUCTURES
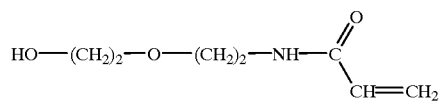
COMPOUND V
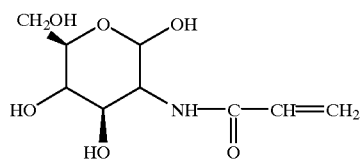
COMPOUND VI
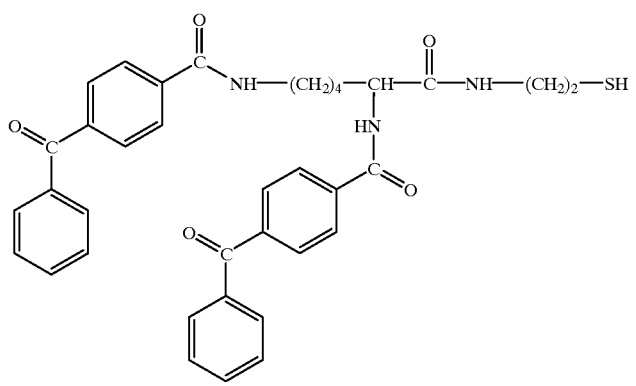
COMPOUND VII
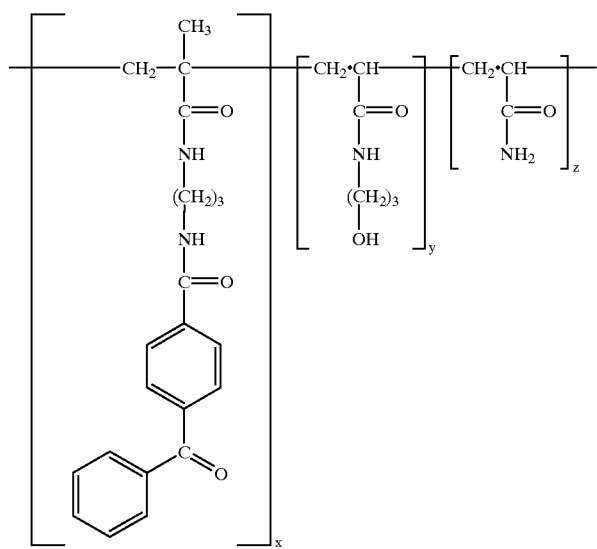
where x = 0 to 5 mole %, y = 5 to 100 mole % and z = 0 to 95 mole %
COMPOUND VIII TABLE OF STRUCTURES
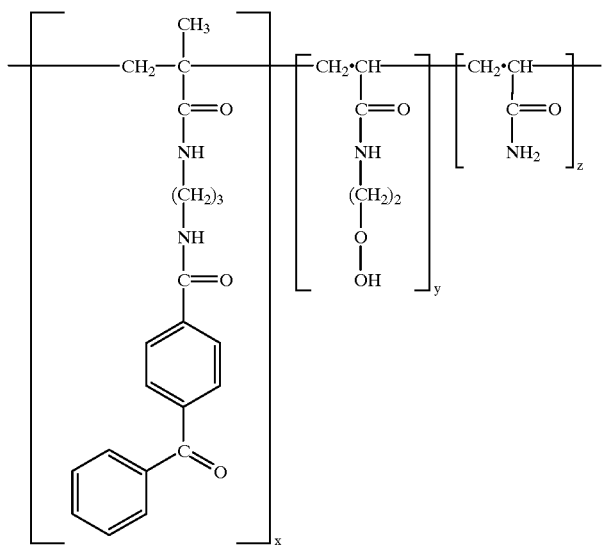
where x = 0 to 5 mole %, y = 5 to 100 mole % and z = 0 to 95 mole %
COMPOUND IX
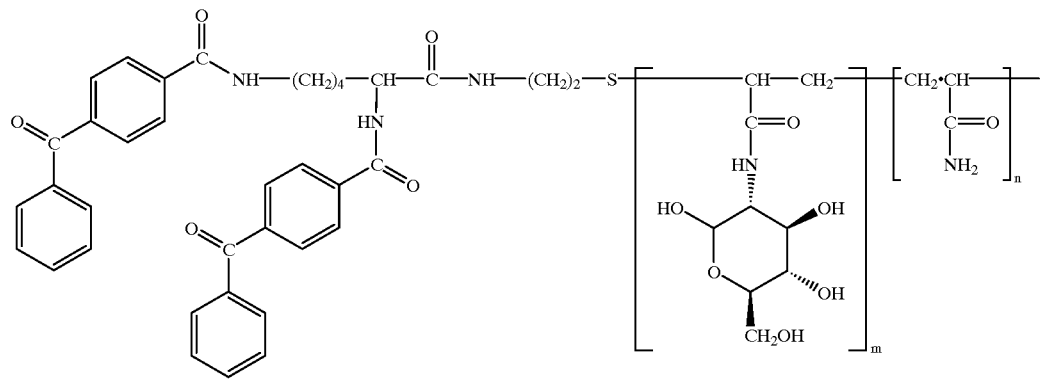
where m = 15 to 45 and n = 50 to 150 (randomly occurring)
COMPOUND X -continued

TABLE OF STRUCTURES

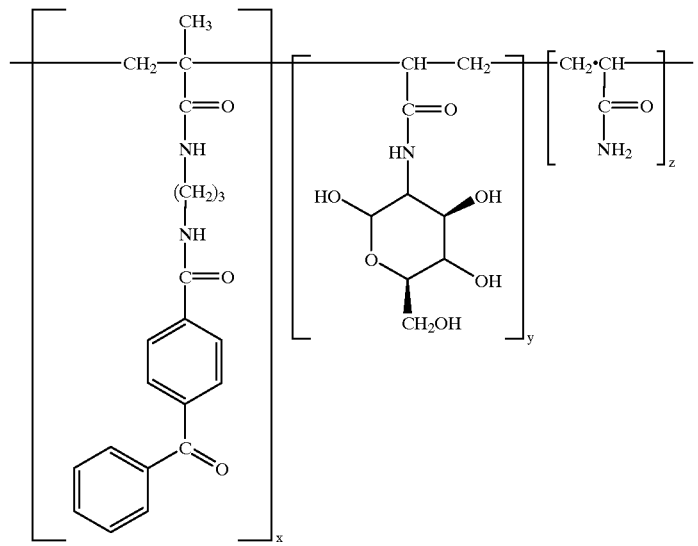

where x = 0 to 5 mole %, y = 5 to 100 mole % and z = 0 to 95 mole %.
COMPOUND XI The following Examples are provided to illustrate, but not limit the present invention. While the invention has been described in terms of its preferred embodiments, those skilled in the art will recognize that the invention can be practiced with modification within the spirit and scope of the appended claims.

EXAMPLES

Example 1

Preparation of 4-Benzoylbenzoyl Chloride (BBA-Cl) (Compound I)

In order to prepare a reactive photogroup, 4-benzoylbenzoic acid (BBA), 1.0 kg (4.42 moles), was added to a dry 5 liter Morton flask equipped with reflux condenser and overhead stirrer, followed by the addition of 645 ml (8.84 moles) of thionyl chloride and 725 ml of toluene. Dimethylformamide, 3.5 ml, was then added and the mixture was heated at reflux for 4 hours. After cooling, the solvents were removed under reduced pressure and the residual thionyl chloride was removed by three evaporations using 3 ×500 ml of toluene. The product was recrystallized from 1:4 toluene: hexane to give 988 g (91% yield) after drying in a vacuum oven. Product melting point was 92–94° C. Nuclear magnetic resonance (NMR) analysis at 80 MHz ($^1$H NMR (CDCl$_3$)) was consistent with the desired product: aromatic protons 7.20–8.25 (m, 9H). All chemical shift values are in ppm downfield from a tetramethylsilane internal standard. The final compound was stored for use in the preparation of a monomer used in the synthesis of photoactivatable polymers as described, for instance, in Example 3.

Example 2

Preparation of N-(3-Aminopropyl)methacrylamide Hydrochloride (APMA) (Compound II)

In order to form an amine-containing monomer intermediate, a solution of 1,3-diaminopropane, 1910 g (25.77 moles), in 1000 ml of CH$_2$Cl$_2$ was added to a 12 liter Morton flask and cooled on an ice bath. A solution of t-butyl phenyl carbonate, 1000 g (5.15 moles), in 250 ml of CH$_2$Cl$_2$ was then added dropwise at a rate which kept the reaction temperature below 15° C. Following the addition, the mixture was warmed to room temperature and stirred 2 hours. The reaction mixture was diluted with 900 ml of CH$_2$Cl$_2$ and 500 g of ice, followed by the slow addition of 2500 ml of 2.2 N NaOH. After testing to insure the solution was basic, the product was transferred to a separatory funnel and the organic layer was removed and set aside as extract #1. The aqueous was then extracted with 3×1250 ml of CH$_2$Cl$_2$, keeping each extraction as a separate fraction. The four organic extracts were then washed successively with a single 1250 ml portion of 0.6 N NaOH beginning with fraction #1 and proceeding through fraction #4. This wash procedure was repeated a second time with a fresh 1250 ml portion of 0.6 N NaOH. The organic extracts were then combined and dried over Na$_2$SO$_4$. Filtration and evaporation of solvent to a constant weight gave 825 g of N-mono-t-BOC-1,3-diaminopropane which was used without further purification.

A solution of methacrylic anhydride, 806 g (5.23 moles), in 1020 ml of CHCl$_3$ was placed in a 12 liter Morton flask equipped with overhead stirrer and cooled on an ice bath. Phenothiazine, 60 mg, was added as an inhibitor, followed by the dropwise addition of N-mono-t-BOC-1,3-diaminopropane, 825 g (4.73 moles), in 825 ml of CHCl$_3$. The rate of addition was controlled to keep the reaction temperature below 10° C. at all times. After the addition was complete, the ice bath was removed and the mixture was left to stir overnight. The product was diluted with 2400 ml of water and transferred to a separatory funnel. After thorough mixing, the aqueous layer was removed and the organic layer was washed with 2400 ml of 2 N NaOH, insuring that the aqueous layer was basic. The organic layer was then dried over $Na_2SO_4$ and filtered to remove drying agent. A portion of the $CHCl_3$ solvent was removed under reduced pressure until the combined weight of the product and solvent was approximately 3000 g. The desired product was then precipitated by slow addition of 11.0 liters of hexane to the stirred $CHCl_3$ solution, followed by overnight storage at 4° C. The product was isolated by filtration and the solid was rinsed twice with a solvent combination of 900 ml of hexane and 150 ml of $CHCl_3$. Thorough drying of the solid gave 900 g of N-[N'-(t-butyloxycarbonyl)-3-aminopropyl]-methacrylamide, m.p. 85.8° C. by differential scanning calorimetry (DSC). Analysis on an NMR spectrometer was consistent with the desired product: $^1H$ NMR ($CDCl_3$) amide NH's 6.30–6.80, 4.55–5.10 (m, 2H), vinyl protons 5.65, 5.20 (m, 2H), methylenes adjacent to N 2.90–3.45 (m, 4H), methyl 1.95 (m, 3H), remaining methylene 1.50–1.90 (m, 2H), and t-butyl 1.40 (s, 9H).

A 3-neck, 2 liter round bottom flask was equipped with an overhead stirrer and gas sparge tube. Methanol, 700 ml, was added to the flask and cooled on an ice bath. While stirring, HCl gas was bubbled into the solvent at a rate of approximately 5 liters/minute for a total of 40 minutes. The molarity of the final HCl/MeOH solution was determined to be 8.5 M by titration with 1 N NaOH using phenolphthalein as an indicator. The N-[N'-(t-butyloxycarbonyl)-3-aminopropyl] methacrylamide, 900 g (3.71 moles), was added to a 5 liter Morton flask equipped with an overhead stirrer and gas outlet adapter, followed by the addition of 1150 ml of methanol solvent. Some solids remained in the flask with this solvent volume. Phenothiazine, 30 mg, was added as an inhibitor, followed by the addition of 655 ml (5.57 moles) of the 8.5 M HCl/MeOH solution. The solids slowly dissolved with the evolution of gas but the reaction was not exothermic. The mixture was stirred overnight at room temperature to insure complete reaction. Any solids were then removed by filtration and an additional 30 mg of phenothiazine were added. The solvent was then stripped under reduced pressure and the resulting solid residue was azeotroped with 3×1000 ml of isopropanol with evaporation under reduced pressure. Finally, the product was dissolved in 2000 ml of refluxing isopropanol and 4000 ml of ethyl acetate were added slowly with stirring. The mixture was allowed to cool slowly and was stored at 4° C. overnight. Compound II was isolated by filtration and was dried to constant weight, giving a yield of 630 g with a melting point of 124.7° C. by DSC. Analysis on an NMR spectrometer was consistent with the desired product: $^1H$ NMR ($D_2O$) vinyl protons 5.60, 5.30 (m, 2H), methylene adjacent to amide N 3.30 (t, 2H), methylene adjacent to amine N 2.95 (t, 2H), methyl 1.90 (m, 3H), and remaining methylene 1.65–2.10 (m, 2H). The final compound was stored for use in the preparation of a monomer used in the synthesis of photoactivatable polymers as described, for instance, in Example 3.

Example 3

Preparation of N-[3-(4-Benzoylbenzamido)propyl] methacrylamide (BBA-APMA) (Compound III)

The reactive photogroup of Example 1 and amine monomer of Example 2 were reacted (via an amide linkage) to form a photogroup-containing monomer in the following manner. Compound II 120 g (0.672 moles), prepared according to the general method described in Example 2, was added to a dry 2 liter, three-neck round bottom flask equipped with an overhead stirrer. Phenothiazine, 23–25 mg, was added as an inhibitor, followed by 800 ml of chloroform. The suspension was cooled below 10° C. on an ice bath and 172.5 g (0.705 moles) of Compound I, prepared according to the general method described in Example 1, were added as a solid. Triethylamine, 207 ml (1.485 moles), in 50 ml of chloroform was then added dropwise over a 1–1.5 hour time period. The ice bath was removed and stirring at ambient temperature was continued for 2.5 hours. The product was then washed with 600 ml of 0.3 N HCl and 2×300 ml of 0.07 N HCl. After drying over sodium sulfate, the chloroform was removed under reduced pressure and the product was recrystallized twice from 4:1 toluene: chloroform using 23–25 mg of phenothiazine in each recrystallization to prevent polymerization. Typical yields of Compound III were 90% with a melting point of 147–151° C. Analysis on an NMR spectrometer was consistent with the desired product: $^1H$ NMR ($CDCl_3$) aromatic protons 7.20–7.95 (m, 9H), amide NH 6.55 (broad t, 1H), vinyl protons 5.65, 5.25 (m, 2H), methylene adjacent to amide N's 3.20–3.60 (m, 4H), methyl 1.95 (s, 3H), and remaining methylene 1.50–2.00 (m, 2H). The final compound was stored for use in the synthesis of photoactivatable polymers as described, for instance, in Examples 8–11 and 13.

Example 4

Preparation of N-(3-hydroxypropyl)acrylamide (HPA) (Compound IV)

A monomer containing a functional group in the form of a hydroxyl group was prepared in the following manner. Acryloyl chloride, 53 ml (0.66 mole) was cooled to −40° C. in a three neck round bottom flask immersed in a isopropanol/dry ice bath. The flask was equipped with an addition funnel, a thermometer and argon inlet. Ethanol (1000 ml) was cooled to −40° C. and added to the cold acryloyl chloride. 3-Amino-1-propanol, 100 ml (1.3 mole) was dissolved in 1000 ml of ethanol. This solution was transferred to the addition funnel and added to the acryloyl chloride dropwise. The solution was stirred in the ethanol/dry ice bath for two hours, followed by stirring overnight at 4° C. The solvent was evaporated. After adding 25 mg of phenothiazine the residue was dissolved in chloroform and purified on silica gel. After washing with chloroform, the product was eluted with acetone, which yielded 69.1 gin (82% yield).

Example 5

Preparation of N-(2-Ethoxy-(2-hydroxyethyl)) acrylamide (HEEA) (Compound V)

Another monomer containing a hydroxyl group was prepared by essentially the same procedure as in Example 4, except that 40.4 ml (0.5 mole) of acryloyl chloride was reacted with 100.2 ml (1.0 mole) of 2-(2-aminoethoxy) ethanol. The compound was eluted from silica gel with acetone to give 94.6 gm (119% yield).

Example 6

Preparation of N-Acrylamido-D-glucosamine (AGA) (Compound VI)

Another alternative monomer containing a functional group in the form of a hydroxyl group was prepared in the following manner. Glucosamine hydrochloride 10.0 g, (0.0464 moles) was added to 12 ml of 3.8-M sodium hydroxide. Potassium carbonate 0.30 g, (0.0022 moles) and sodium nitrite 0.35 g, (0.0051 moles) were then added and the mixture was stirred until a clear solution was obtained. To the clear solution was added 10-ml chloroform, and the mixture was stirred vigorously while in an ice bath. A solution of acryloyl chloride 4.45g, (4.0 ml; 0.0492 moles) in 5 ml of chloroform was added in 100 microliter portions with alternate additions of 55 μl of 10 N sodium hydroxide (4.95 ml total) with stirring in an ice bath. The stirring was continued for 30 minutes after the additions were complete. The chloroform was removed. The pH was adjusted to 3 followed by 3×10-ml extractions of chloroform to remove acrylic acid. The water solution was stored at ~4° C. The use of AGA in polymerization is described in Examples 12 and 13.

Example 7

Preparation of N-(2-Mercaptoethyl)-2,6-bis(4-benzoylbenzamido)hexanamide (Compound VII)

A photoactivatable chain transfer reagent was prepared in the following manner. Lysine monohydrochloride, 3.65 g (20 mmol), was dissolved in 8 ml of 2 N sodium hydroxide and cooled in an ice bath. A solution of 10.77 g (44 mmol) 4-benzoylbenzoyl chloride, prepared according to the general method described in Example 1, in 17 ml of chloroform was added simultaneously with 4.48 g of sodium hydroxide in 19 ml of water. The reaction was stirred on the ice bath for 2 hours and then was allowed to warm to room temperature for 3 hours. Hydrochloric acid was used to adjust the pH to 1 and an additional 60 ml of chloroform were added. A centrifuge was used to separate the layers and the aqueous was extracted with 3×50 ml of chloroform. The combined organic extracts were dried over sodium sulfate. An attempt was made to recrystallize the resulting solid product from 80% acetic acid but the recovery of product was poor. The mother liquors were diluted with water to precipitate the product, which was then dissolved in chloroform, washed with 10% sodium bicarbonate, 1 N hydrochloric acid, and finally water. The solution was dried over sodium sulfate and the product was used without purification. Analysis on an NMR spectrometer was consistent with the desired product: $^1$H NMR ($CDCl_3$) acid proton 8.45 (broad s, 1H), aromatic and amide protons 7.00–8.10 (m, 20H), CH 4.50–4.90 (m, 1H), methylene adjacent to N 3.30–3.70 (m, 2H), remaining methylenes 1.10–2.25 (m, 6H).

The lysine derivative, 4.35 g (7.73 mmol), and N-hydroxysuccinimide, 0.901 g (7.83 mmol), were dissolved in 40 ml of dry 1,4-dioxane, followed by the addition of 1.951 g (9.45 mmol) of 1,3-dicyclohexylcarbodiimide (DCC) in 10 ml of 1,4-dioxane. The mixture was allowed to stir overnight at room temperature. The resulting white solid was filtered off and washed with 2×25 ml of 1,4-dioxane. The solvent was removed under reduced pressure and the residue was rinsed with 3×25 ml of hexane to remove excess DCC. The resulting N-oxysuccinimide (NOS) ester, 4.10 g (81% yield), was used without further purification.

2-Aminoethanethiol hydrochloride, 0.75 g (6.6 mmol), was diluted with 15 ml of chloroform and 1.09 ml of triethylamine under an argon atmosphere. The NOS ester, 4.10 g (6.22 mmol), in 25 ml of chloroform was added dropwise at room temperature over a 30 minute period. After 4 hours of reaction, the mixture was washed with water and 0.05 N hydrochloric acid, followed by drying over sodium sulfate. The product was purified using silica gel flash chromatography using a 95:5 $CHCl_3$: $CH_3OH$ solvent system to give 2.30 g of product, a 59% yield. Analysis on an NMR spectrometer was consistent with the desired product: $^1$H NMR ($CDCl_3$) aromatic and amide protons 6.90–8.00 (m, 21H), CH 4.40–4.85 (m, 1H), methylenes adjacent to N 3.00–3.75 (m, 4H), remaining methylenes 1.00–2.95 (m, 8H), and SH 1.40 (t, 1H).

Example 8

Preparation of a Copolymer of Acrylamide, BBA-APMA, and (HPA) (Random Photo PA-HPA) (Compound VIII)

A photoactivatable copolymer of the present invention was prepared in the following manner. Acrylamide 1.69 g (23.8 mmol), for use as a "diluent" monomer as described herein, was dissolved in 43.5 ml of DMSO along with 0.17 g (0.49 mmol) of BBA-AMPA (photogroup-containing monomer, Compound III), prepared according to the general method described in Example 3, 3.14 g (24.3 mmol) HPA (an OH-containing monomer, Compound IV), prepared according to the general method described in Example 4, 0.10 g (0.58 mmol) of 2,2'-azobisisobutyronitrile (AIBN), and 0.049 ml (0.32 mmol) of N,N,N',N'-tetramethylethylenediamine (TEMED). The solution was deoxygenated with a helium sparge for 4 minutes. The headspace was replaced with argon, and the vessel was sealed for an overnight heating at 55° C. The reaction solution was placed in dialysis tubing (12–14,000 MWCO), and dialyzed against DI water for 5 days. The water solution was lyophilized to give 4 g white solid with a photo load of 0.094 μmole/mg (theory 0.097 μmole/mg).

Example 9

Preparation of a Copolymer of BBA-APMA, and (HPA) (Random Photo HPA)(Compound VIII)

A photoactivatable copolymer of the present invention was prepared in the following manner (and without the use of a "diluent" monomer such as acrylamide). BBA-AMPA (Compound III), prepared according to the general method described in Example 3, 0.17 g (0.49 mmol) was dissolved in 33 ml of DMSO along with 4.87 g (37.73 mmol) HPA (Compound IV), prepared according to the general method described in Example 4, 0.08 g (0.46 mmol) of AIBN, and 0.038 ml (0.25 mmol) of TEMED. The solution was deoxygenated with a helium sparge for 4 minutes. The headspace was replaced with argon, and the vessel was sealed for an overnight heating at 55° C. The reaction solution was placed in dialysis tubing (12–14,000 MWCO), and dialyzed against DI water for 5 days. The water solution was lyophilized to give 4.27 g of white solid with a photo load of 0.073 μmole/mg (theory 0.076 μmole/mg).

Example 10

Preparation of a Copolymer of Acrylamide, BBA-APMA, and (HEEA) (Random Photo PA-HEEA) (Compound IX)

A photoactivatable copolymer of the present invention was prepared in the following manner. Acrylamide 1.48 g (20.8 mmol) was dissolved in 37.3 ml of DMSO along with 0.15 g (0.42 mmol) of BBA-AMPA (Compound III), prepared according to the general method described in Example 3, 3.38 g (21.2 mmol) HEEA (Compound V), prepared according to the general method described in Example 5, 0.084 g (0.51 mmol) of AIBN, and 0.043 ml (0.28 mmol) of TEMED. The solution was deoxygenated with a helium sparge for 4 minutes. The headspace was replaced with argon, and the vessel was sealed for an overnight heating at 55° C. The reaction solution was placed in dialysis tubing (12–14,000 MWCO), and dialyzed against DI water for 5 days. The water solution was lyophilized to give 3.7 g white solid with a photo load of 0.092 µmole/mg (theory 0.085 µmole/mg)

Example 11

Preparation of a Copolymers of BBA-APMA and (HEEA) (Random Photo HEEA)(Compounds IX)

A photoactivatable copolymer of the present invention was prepared in the following manner. BBA-APMA (Compound III), prepared according to the general method described in Example 3, 0.11 g (0.31 mmol) was dissolved in 26 ml of DMSO along with 4.89 g (30.72 mmol) HEEA (Compound V), prepared according to the general method described in Example 5, 0.06 g (0.37 mmol) of AIBN, and 0.031 ml (0.21 mmol) of TEMED. The solution was deoxygenated with a helium sparge for 4 minutes. The headspace was replaced with argon, and the vessel was sealed for an overnight heating at 55° C. The reaction solution was placed in dialysis tubing (12–14,000 MWCO), and dialyzed against DI water for 6 days. The water solution was lyophilized to give 4.35 g of white solid designated as compound IX with a photo load of 0.061 µmole/mg (theory 0.062 µmole/mg).

Using the above procedure, a compound similar to that described in the previous paragraph was made, but crude HEEA was used in place of the purified HEEA. The following ingredient charge was used to give the photo HEEA (Compound IX). BBA-AMPA (Compound III), prepared according to the general method described in Example 3, 0.043 g (0.12 mmol) was dissolved in 10.4 ml of DMSO along with 1.96 g (12.29 mmol) HEEA (Compound V), prepared according to the general method described in Example 5, 0.024 g (0.15 mmol) of AIBN, and 0.012 ml (0.083 mmol) of TEMED. The solution was deoxygenated with a helium sparge for 4 minutes. The headspace was replaced with argon, and the vessel was sealed for an overnight heating at 55° C. The reaction solution was placed in dialysis tubing (12–14,000 MWCO), and dialyzed against DI water for 6 days. The water solution was lyophilized to give 1.33 g of white solid designated as compound IX with a photo load of 0.078 µmole/mg (theory 0.062 µmole/mg).

Example 12

Preparation of an End Point Photo Glucosamine Polymer (End-point Di-BBA-AGA)(Compound X)

Acrylamide (400mg, 5.6 mmole) was dissolved in 10 ml of dimethylsulfoxide(DMSO). To that solution was added 400 mg (1.48 mmole) of N-acryloylglucosamine (Compound VI). Additionally were added 34 mg of N-(2-mercaptoethyl)-2,6-bis(4-benzoylbenzamido)hexanamide, 200 mg of AIBN and 50 µl of TEMED. The solution was sparged with nitrogen, then placed in a 55° C. oven overnight. The resulting polymer solution was dialyzed against deionized water using SpectraPor 1 (Spectrum) dialysis membrane. After dialysis, the solution was lyophilized. The dried polymer obtained was 0.58 gm by weight. At 0.1 mg/ml in deionized water, the polymer had an absorbance at 265 nm of 0.202.

Example 13

Preparation of a Copolymer of Acrylamide, BBA-APMA, and AGA (Random Photo PA-AGA) (Compound XI)

To a solution of 200 mg (0.74 mmole) N-acryloylglucosamine (Compound VI) in 5 ml of DMSO was added 500 mg of acrylamide (7.0 mmole) and 98 mg of BBA-APMA (0.28 mmole Compound III), 50 mg of azobiscyanovalerate and 100 µl of TEMED. The solution was sparged with nitrogen, then placed in a 55° C. oven overnight. The polymer was dialyzed against deionized water, then lyophilized.

Example 14

Preparation of a PolyHPA-coated Surface

A polymer of HPA is prepared using HPA monomer synthesized according to Example 4 and a polymerization reaction following the procedure of Example 9 except omitting the BBA-APMA. The lyophilized polymer is dissolved in a solution of 1,1'-carbonyldiimidazole in formamide and allowed to react for one hour. Glass slides are coated with aminopropyltrimethoxysilane, washed and dried. The activated polyHPA solution is applied to the amine-modified slides and incubated for one hour. The slides are then immersed in 0.1M sodium carbonate solution containing 0.1M ethanolamine for one hour to block or hydrolyze remaining carbonylimidazole groups. The slides are then washed in deionized water and dried.

Example 15

Preparation of a PhotopolyHEEA-coated Surface

A copolymer of HEEA (Compound V) and BBA-APMA (Compound III), prepared according to Example 10, is dissolved in deionized water at 2.0 mg/ml. Polystyrene microscope slides are dipped into the polymer solution, then placed on a flat surface and illuminated for one minute while still wet, using a Dymax lighting system having a 400 watt medium pressure mercury bulb at a distance such that the illumination intensity is approximately 2.0 mW/cm$^2$ at 330–340 nm wavelength. The slides are then washed with deionized water and dried.

What is claimed is:

1. A method for performing solid phase synthesis, the method comprising the steps of:

a) providing a support material providing a surface adapted for use in combinatorial synthesis, b) providing a polymeric reagent formed by the polymerization of monomers of the formula:

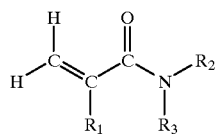

wherein $R_1$ represents hydrogen or $C_1$–$C_6$ alkyls, and wherein $R_2$ and $R_3$, independently among them, represent hydrogen, $C_1$–$C_6$ alkyls or phenyls containing one or more reactive substituents selected from

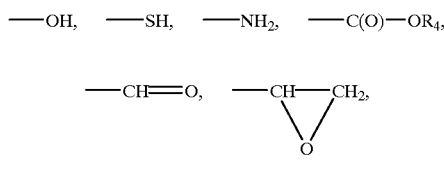

$OR_5$, or $SR_5$ (where $R_4$ is a $C_1$–$C_6$ alkyl or a heterocyclic ring containing one or more nitrogen atoms and $R_5$ is a $C_1$–$C_6$ alkyl or phenyl containing one or more reactive substituents selected from

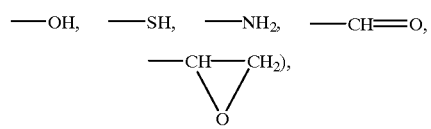

c) applying the reagent to the support surface and covalently attaching the polymeric reagent to the support surface, d) providing a first reactive monomer selected from nucleotides and amino acids, the monomer comprising a corresponding group thermochemically reactive with the bound reactive substituent, e) contacting and reacting the first monomer with the polymeric reagent upon the support surface under conditions suitable to react the corresponding group with the bound reactive substituent, thus providing a growing polymeric chain, and f) providing and sequentially attaching subsequent monomers to the growing polymeric chain to obtain a desired polymeric product.

2. A method according to claim 1 wherein the resultant polymeric product is retained and used in situ.

3. A method according to claim 1 wherein the resultant polymeric product is cleaved and removed from its position upon the support.

4. A method according to claim 1 wherein the polymeric product is selected from the group consisting of polynucleotides, polysaccharides, and polypeptides.

5. A method according to claim 1 wherein the support is provided in the form of a bead, wafer, film, disc or plate.

6. A method according to claim 5 wherein the support comprises a material selected from organosilane-treated glass, organosilane-treated silicon, polypropylene, polyethylene, and polystyrene.

7. A method according to claim 1 wherein the polymeric reagent is of the formula:

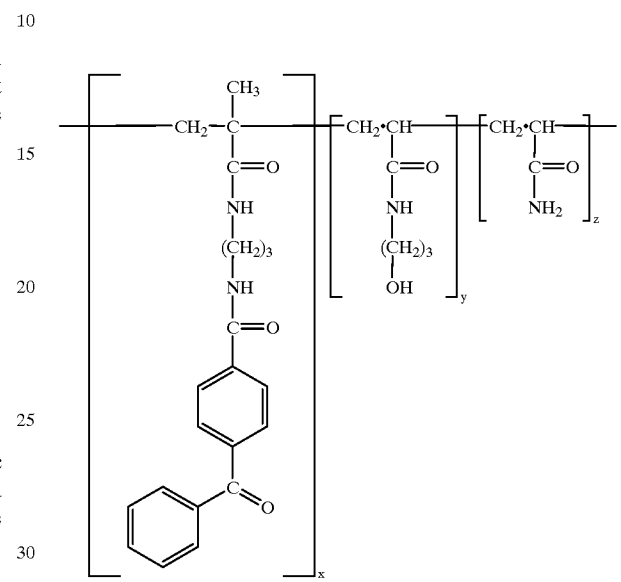

where X = 0–5 mole %, Y = 5–100 mole % and Z = 0–95 mole%.

8. A method according to claim 1 wherein the polymeric reagent is of the formula:

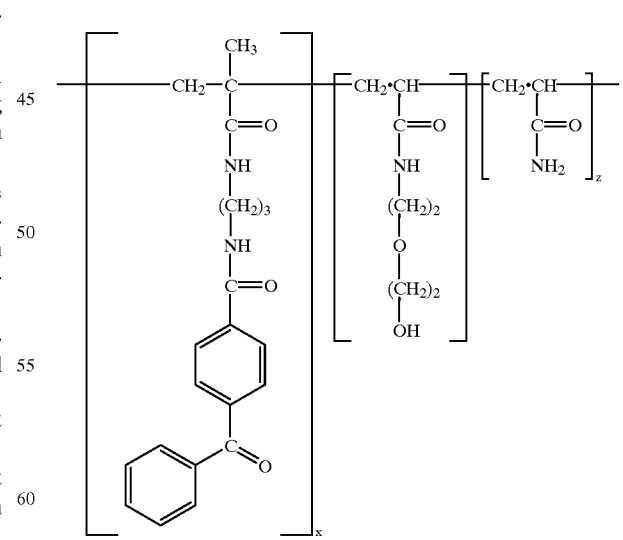

where x = 0–5 mole %, y = 5–100 mole % and z = 0–95 mole%.

9. A method according to claim 1 wherein the polymeric reagent is of the formula:

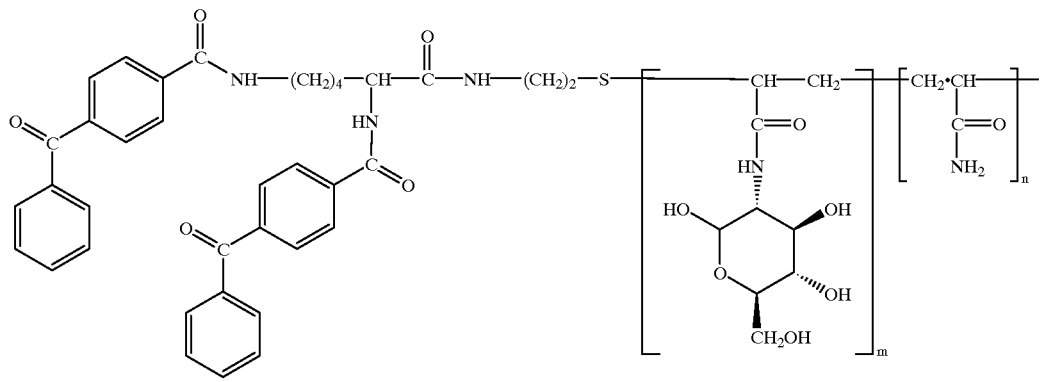

where m = 15–45 and n = 50–150.

10. A method according to claim 1 wherein the polymeric reagent is of the formula:

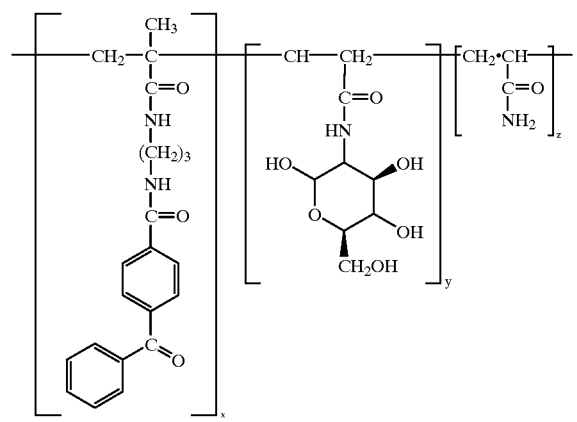

where x = 0–5 mole %, y = 5–100 mole % and z = 0–95 mole%.

11. A polymer-coupled support comprising:

(a) a polymeric reagent composition prepared by the polymerization of one or more of the monomers of the formula:

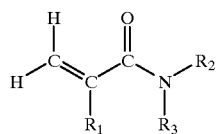

wherein $R_1$ represents hydrogen or $C_1$–$C_6$ alkyls, and wherein $R_2$ and $R_3$, independently among them represent hydrogen, $C_1$–$C_6$ alkyls or phenyls containing one or more reactive substituents selected from

—OH, —SH, —NH$_2$, —C(O)—OR$_4$,

—CH=O, —CH—CH$_2$,
              \\  /
               O $OR_5$, or $SR_5$ (where $R_4$ is a $C_1$–$C_6$ alkyl or a heterocyclic ring containing one or more nitrogen atoms and $R_5$ is a $C_1$–$C_6$ allyl or phenyl containing one or more reactive substituents selected from —OH, —SH, —NH$_2$, —CH=O, —CH—CH$_2$); and
                                      \\  /
                                       O (b) a support wherein the polymeric reagent is directly attached to the support.

12. The polymer-coupled support according to claim 11 wherein the polymeric reagent is of the formula:

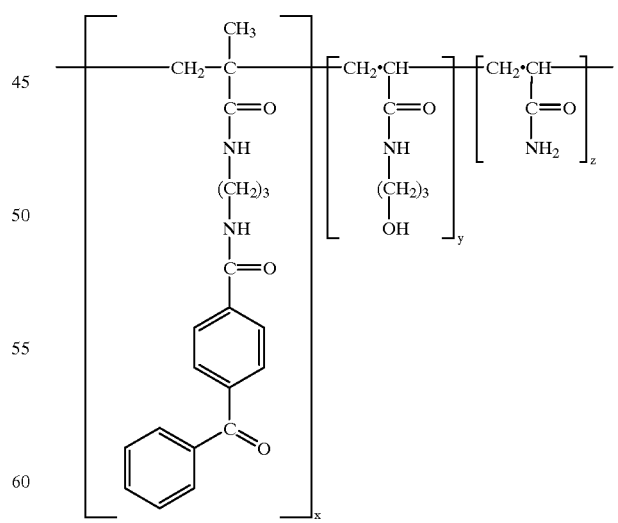

where x = 0 to 5 mole %, y = 5 to 100 mole % and z = 0 to 95 mole%.

13. The polymer-coupled support according to claim 11 wherein the polymeric reagent is of the formula:

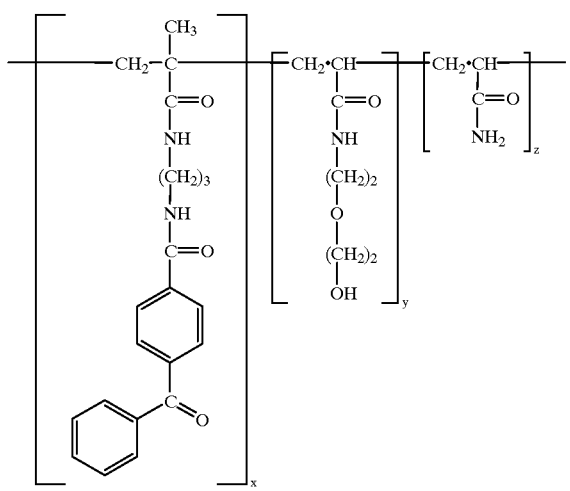

where x = 0 to 5 mole %, y = 5 to 100 mole % and z = 0 to 95 mole%.

14. A polymeric reagent composition of the formula:

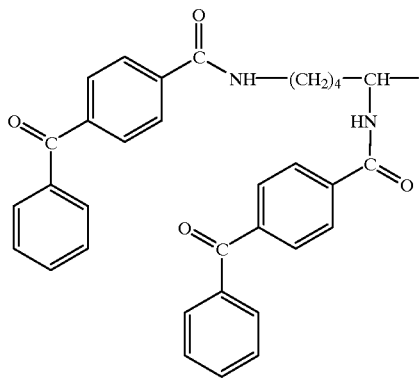

where m = 15 to 45 and n = 50 to 150.

15. A polymeric reagent composition of the formula:

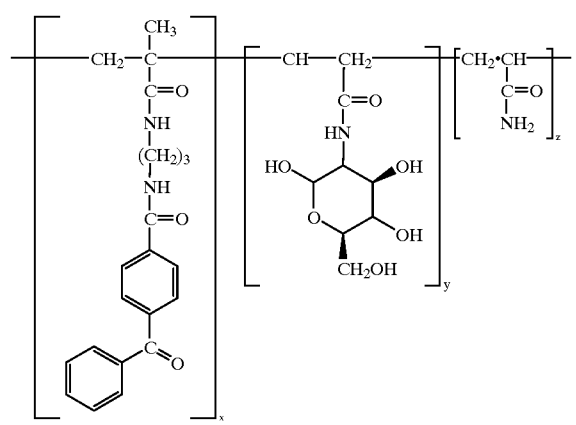

where x = 0 to 5 mole %, y = 5 to 100 mole % and z = 0 to 95 mole%.

16. A method of preparing a polymer-coupled support, the method comprising steps of:

(a) polymerizing monomers of the formula:

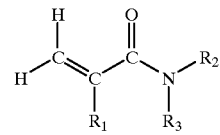

wherein $R_1$ represents hydrogen or $C_1$–$C_6$ alkyls, and wherein $R_2$ and $R_3$, independently among them, represent hydrogen, $C_1$–$C_6$ alkyls or phenyls containing one or more reactive substituents selected from

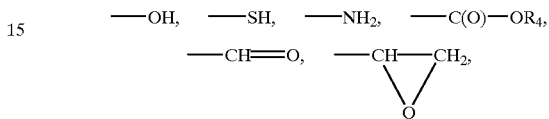

$OR_5$, or $SR_5$ (where $R_4$ is a $C_1$–$C_6$ alkyl or a heterocyclic ring containing one or more nitrogen atoms and $R_5$ is a $C_1$–$C_6$ alkyl or phenyl containing one or more reactive substituents selected from

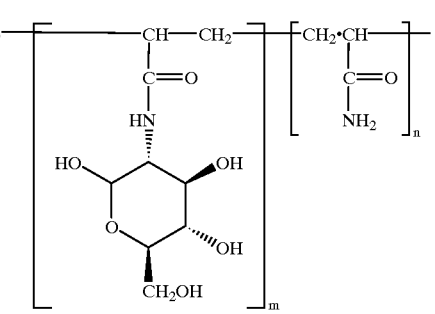

to form a polymeric reagent; and (b) attaching the polymeric reagent directly to a support.

17. The polymer-coupled support according to claim 11 wherein the polymeric reagent is directly attached to the support via one or more of the reactive substituents of $R_2$ or $R_3$.

18. The polymer-coupled support according to claim 11 wherein the polymeric reagent comprises a photoreactive group.

19. The polymer-coupled support according to claim 11 wherein the support material is selected from the group consisting of organosilane-treated glass and organosilane-treated silicon.

20. The polymer-coupled support according to claim 11 wherein the support material is selected from the group consisting of polypropylene, polyethylene, and polystyrene.

21. The polymer-coupled support according to claim 11 wherein the support is selected from the group consisting of polyacrylamide beads, latex beads, dimethacrylamide beads, and glass particles coated with hydrophobic polymers.

22. The polymer-coupled support according to claim 11 wherein the polymeric reagent is configured and arranged for solid phase synthesis of a polymer selected from the group consisting of peptides, oligonucleotides, and peptide nucleic acids.

23. The polymer-coupled support according to claim 11 wherein the polymeric reagent is configured and arranged for solid phase synthesis of a compound selected from the group consisting of nonpolymeric organic compounds.

* * * * *